(12) United States Patent
Kohn et al.

(10) Patent No.: US 7,838,122 B2
(45) Date of Patent: Nov. 23, 2010

(54) HYDRAZIDE COMPOUNDS WITH ANGIOGENIC ACTIVITY

(75) Inventors: Joachim B. Kohn, Piscataway, NJ (US); Kristen S. Labazzo, North Brunswick, NJ (US); Durgadas Bolikal, Edison, NJ (US)

(73) Assignee: Rutgers, the State University of New Jersey, New Brunswick, NJ (US)

( * ) Notice: Subject to any disclaimer, the term of this patent is extended or adjusted under 35 U.S.C. 154(b) by 225 days.

(21) Appl. No.: 12/116,087

(22) Filed: May 6, 2008

(65) Prior Publication Data

US 2008/0274158 A1  Nov. 6, 2008

Related U.S. Application Data

(62) Division of application No. 11/001,250, filed on Dec. 1, 2004, now Pat. No. 7,368,169.

(60) Provisional application No. 60/526,061, filed on Dec. 1, 2003.

(51) Int. Cl.
*C08G 65/333* (2006.01)
*C08F 8/30* (2006.01)

(52) U.S. Cl. .................. 428/474.4; 428/500; 428/532; 525/61; 525/376; 525/409; 525/420; 527/312; 528/208; 528/421; 424/78.08; 424/78.17; 424/78.18; 424/78.36; 424/78.37; 424/78.38; 424/426; 606/77; 623/23.75

(58) Field of Classification Search ........................ None
See application file for complete search history.

(56) References Cited

U.S. PATENT DOCUMENTS

| 4,115,305 | A | * | 9/1978 | Hornby et al. | .............. 525/54.1 |
| 4,371,673 | A | * | 2/1983 | Pitha | ........................... 525/426 |
| 5,099,060 | A | | 3/1992 | Kohn et al. | |
| 5,198,507 | A | | 3/1993 | Kohn et al. | |
| 5,216,115 | A | | 6/1993 | Kohn et al. | |
| 5,587,507 | A | | 12/1996 | Kohn et al. | |
| 5,670,602 | A | | 9/1997 | Kohn et al. | |
| 6,048,521 | A | | 4/2000 | Kohn et al. | |
| 6,103,255 | A | | 8/2000 | Levene et al. | |
| 6,261,585 | B1 | | 7/2001 | Sefton et al. | |
| 6,284,862 | B1 | | 9/2001 | Kohn et al. | |
| 6,319,492 | B1 | | 11/2001 | Kohn et al. | |
| 6,494,908 | B1 | * | 12/2002 | Huxel et al. | ................. 623/1.22 |
| 2002/0049281 | A1 | | 4/2002 | Zhao et al. | |

FOREIGN PATENT DOCUMENTS

| CA | 2078712 | * | 3/1993 |
| JP | 2001064385 | | 3/2001 |
| WO | WO 98/05363 | * | 2/1998 |

OTHER PUBLICATIONS

Benzina et al., A versatile three-iodine molecular building block leading to new radiopaque polymeric biomaterials, Journal of Biomedical Materials Research, Nov. 1, 1996, pp. 459-466, vol. 32, John Wiley & Sons, Inc., US.
Vercruysse, "Synthesis and in Vitro Degradation of New Polyvalent Hydrazide Crosslinked Hydrogels of Hyaluronic Acid", Bioconjugate Chemistry, 1997, vol. 8 p. 686-694.
Derwent Abstract of IL 60569A, Apr. 30, 1984.
Pine; Organic Chemistry, 4th Edition, 1980, pp. 785-787.
Nathan et al.; Hydrogels Based on Water-Soluble Poly(ether urethanes) Derived from L-Lysine and Poly(ethylene glycol), Macromolecules, 1992, 25, 4476.

* cited by examiner

*Primary Examiner*—David Buttner
(74) *Attorney, Agent, or Firm*—Fox Rothschild LLP

(57) ABSTRACT

Compounds exhibiting angiogenic properties incorporating the structure of Formula I:

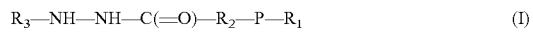

$$R_3—NH—NH—C(=O)—R_2—P—R_1 \quad (I)$$

wherein P is a water-soluble, biodegradable polymer, $R_1$ is hydrogen, lower alkyl, lower alkoxy or —$R_2$—C(=O)—NH—NH—$R_3$; each $R_2$ is independently —$CH_2$—, —NH— or O; and each $R_3$ is independently hydrogen or a residue of a naturally occurring alpha-L-amino acid or dipeptide thereof. Polymer networks crosslinked with hydrazide compounds are also disclosed, together with implantable medical devices incorporating the compounds and crosslinked polymers, and angiogenesis-promoting treatment methods, including wound-treatment methods.

7 Claims, 8 Drawing Sheets

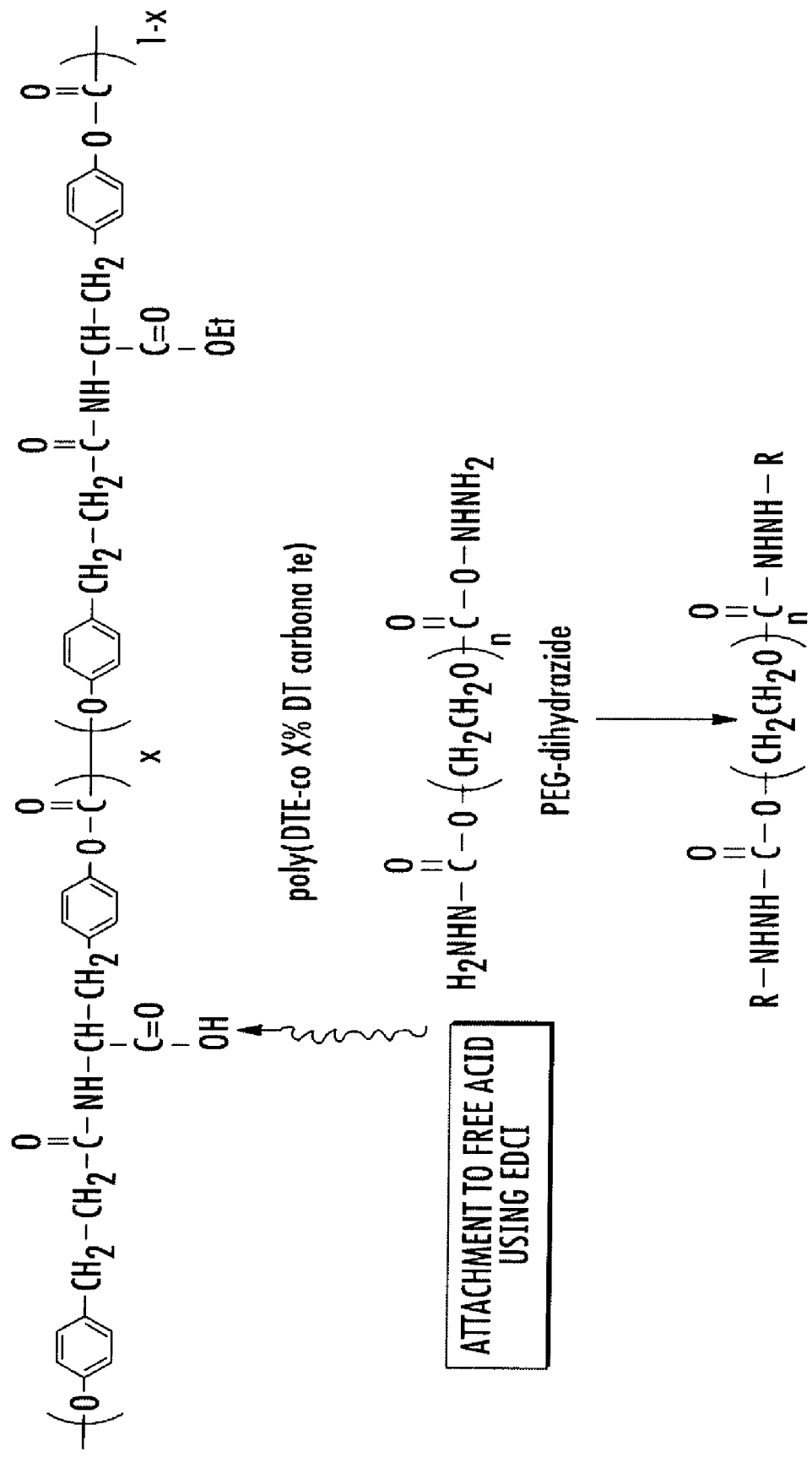
FIG. 2  FINAL CROSSLINKED PRODUCT, WHERE R=poly(DTE-co X% DT carbonate)

HYDRAZIDE COMPOUNDS WITH ANGIOGENIC ACTIVITY

CROSS-REFERENCE TO RELATED APPLICATIONS

The present application is a divisional of U.S. application Ser. No. 11/001,250, filed Dec. 1, 2004, now U.S. Pat. No. 7,368,169, which claims priority benefit under 35 U.S.C. §119(e) of U.S. Provisional Application No. 60/526,061, filed Dec. 1, 2003, the disclosures of which are incorporated herein by reference.

BACKGROUND OF THE INVENTION

The present invention relates to hydrazide compounds with angiogenic activity. In particular, the present invention relates to angiogenic water-soluble, biodegradable polymers having a terminal hydrazide group on one or both end optionally linking the polymer to a residue of a naturally-occurring alpha-L-amino acid or a dipeptide thereof. The present invention also relates to polymer networks cross-linked via the hydrazide-terminal polymers of the invention, and to the use of the hydrazide compounds and polymer networks of the present invention to promote angiogenesis.

Synthetic, degradable polymers are currently being evaluated as medical implants in a wide range of applications, such as orthopedic bone fixation devices, drug delivery systems, cardiovascular implants, and scaffolds for the regeneration of tissue. Blood vessels are a pre-requisite to a functional, implanted tissue engineered device and implanted devices often fail to be incorporated into body tissue due to insufficient angiogenesis, that is, lack of formation of new blood vessels from a pre-existing vascular bed, which provides the necessary blood supply to the implant.

Attempts have been made to improve the level of angiogenesis in implanted tissue regeneration scaffolds by the use of biological molecules such as angiogenesis promoters, cytokines, and growth factors. While often effective, these biological compounds are expensive and not fully characterized with regard to their toxicity. Angiogenesis is a complex and highly biologically regulated process involving a coordinated sequence of endothelial cell division, degradation of vascular basement membrane and surrounding extracellular matrix with migration of endothelial cells. Under normal conditions angiogenesis is seen in the female reproductive system and wound healing whereas abnormal angiogenesis may contribute to tumor neovascularization, psoriasis, endometriosis or arthritis. In tissue engineering, angiogenesis is crucial to encourage cellular growth into a tissue regeneration scaffold and to ensure the development of functional tissue within the scaffold by providing adequate nutrients and oxygen to the device.

Several strategies have been employed to induce vascularization of a scaffold by incorporating biological moieties including growth factors, or the use of tumorigenic cell lines that will secrete angiogenic substances. U.S. Pat. No. 6,261,585 discloses angiogenic polymeric material that is not inherently angiogenic but rather attracts growth factors to the site of implantation.

Hydrogels are polymeric materials which swell in water without dissolution. Because of their compliance with soft tissue in terms of mechanical properties and high water content, hydrogels have been investigated for use in a wide range of medical applications such as drug delivery systems, contact lenses, surface coatings for blood-contacting materials and wound care products. In the field of tissue engineering, hydrogels have been investigated for the repair of skin, bone, cartilage, tendon and nerves. Both hydrogels obtained from natural materials such as alginate and collagen, and synthetic hydrogels obtained by crosslinking polymers such as poly (ethylene glycol) have been used. In contrast to hydrogels derived from natural materials, synthetic hydrogels often provide greater control over properties such as gelling time, crosslink density, compressive modulus and degradation rate. Biodegradable hydrogels for tissue regeneration are required which resorb over time without the release of toxic degradation products.

Preparation of hydrogels typically requires hydrophilic polymers such as poly(ethylene oxide), block copolymers of poly(ethylene oxide-co-propylene oxide), poly(vinyl alcohol), poly(vinylpyrrolidone), poly(ethyloxazoline), polyamines, poly-aminoamides, polypeptides, polysaccharides, cellulosics such as carboxymethylcellulose and hydroxyethylcellulose, chondroitin sulfate, heparin, alginates, proteins such as collagen or gelatin, and other polymers well known in the art, which are typically crosslinked by ionic or covalent linkages. For example, hydrogels may be formed from polysaccharides crosslinked by monovalent or multivalent cations such as sodium or calcium. Polyethylene oxide-polypropylene glycol block copolymers may be crosslinked by hydrogen bonding. Polyelectrolytes may be crosslinked in aqueous solutions by monvalent or multivalent ions or polyelectrolytes of the opposite charge to form highly swollen hydrogels. The ionic crosslinking groups include phenols, amines, imines, amides, carboxylic acids, sulfonic acids and phosphate groups. Hydrogels may be prepared from precursors polymers such as soluble polyamines that are covalently crosslinked with a water-soluble diisothiocyanate such as polyethylene glycol diisothiocyanate. Polymers with ethylenically unsaturated groups may be crosslinked by free radical reactions typically employing a radical initiator. For example, poly ethylene glycol acrylates may be polymerized using photoinitiators that generate free radicals on exposure to ultraviolet or visible light.

Diphenols are monomeric starting materials for polycarbonates, polyimino-carbonates, polyarylates, polyurethanes, and the like. Commonly owned U.S. Pat. Nos. 5,099,060 and 5,198,507 disclose amino acid-derived diphenol compounds useful in the polymerization of polycarbonates and polyiminocarbonates. The resulting polymers are useful as degradable polymers in general and as tissue-compatible, bioerodible materials for medical uses, in particular. The suitability of these polymers for their end use application is the result of their polymerization from diphenols derived from the naturally occurring amino acid, L-tyrosine. The disclosures of U.S. Pat. Nos. 5,099,060 and 5,198,507 are hereby incorporated by reference. These previously-known polymers are strong, water-insoluble materials.

The same monomeric L-tyrosine derived diphenols are also used in the synthesis of polyarylates as described in commonly owned U.S. Pat. No. 5,216,115 and in the synthesis of poly(alkylene oxide) block copolymers with the aforementioned polycarbonates and polyarylates, which is disclosed in commonly owned U.S. Pat. No. 5,658,995. The disclosures of U.S. Pat. Nos. 5,216,115 and 5,658,995 are also hereby incorporated by reference.

Commonly owned U.S. Pat. No. 6,284,862 discloses dihydroxy monomers prepared from hydroxy acid amides of L-tyrosine that are also useful starting materials in the polymerization of polycarbonates, polyarylates, and the like. The preparation of polycarbonates and polyarylates from these monomers is also disclosed. The disclosure of U.S. Pat. No. 6,284,862 is also hereby incorporated by reference.

The foregoing monomers can be used to polymerize essentially any polymer capable of being derived from a diphenol or a dihydroxy monomer, such as polyethers, polyphosphazines and the like.

There remains a need for a means by which the level of angiogenesis in implanted tissue regeneration scaffolds formed from such polymers and monomers may be improved.

SUMMARY OF THE INVENTION

Hydrazide compounds have now been discovered that induce blood vessels to grow into an implanted, resorbable device, mimicking the biological activity of growth factors such as FGF-β. The blood vessels are necessary for the success of the implant, which will eventually resorb (dissolve) and leave only natural, healthy tissue. The compound can be used in devices for any tissue which require vascularization, such as skin or bone. Additionally, the compound can be used alone, and can be incorporated into almost any device or drug release system, for site-specific or systemic delivery, but at a fraction of the cost of existing pro-angiogenic substances.

Therefore, according to one aspect of the present invention, a compound exhibiting angiogenic properties is provided incorporating the structure of Formula I:

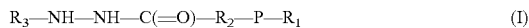

Wherein P is a water-soluble, biodegradable polymer, $R_1$ is hydrogen, lower alkyl, lower alkoxy or —$R_2$—C(=O)—NH—NH—$R_3$; each $R_2$ is independently —$CH_2$—, —NH— or O; and each $R_3$ is independently hydrogen or a residue of a naturally occurring alpha-L-amino acid or dipeptide thereof.

When P is a poly(alkylene oxide) and either $R_1$ and $R_3$ are both hydrogen or $R_1$ is —$R_2$—C(=O)—NH—NH—$R_3$ and both $R_3$'s are hydrogen, the defined compounds are hydrazide-functionalized poly(alkylene oxides), which are commercially-available materials. Thus, while the angiogenic properties discovered for these compounds are heretofore unknown, the compounds themselves are not new. Therefore, compounds of the present invention do not include compounds in which P is a poly(alkylene oxide) when either $R_1$ and $R_3$ are both hydrogen or $R_1$ is —$R_2$—C(=O)—NH—NH—$R_3$ and both $R_3$'s are hydrogen. Such compounds, however, are included among compounds suitable for use in the methods of the present invention.

The Formula I dihydrazide compounds of the present invention in which $R_1$ is —$R_2$—C(=O)—NH—NH—$R_3$ and both $R_3$'s are hydrogen are effective cross-linking agents for a wide variety of backbone polymers. The crosslinked polymers have, as a consequence of the properties of the dihydrazide cross-linking agents, angiogenic properties as well as hydrogel properties. Therefore, according to another aspect of the present invention, crosslinked polymer networks are provided exhibiting angiogenic properties, in which biodegradable polymer chains are crosslinked via hydrazide bonds using the compound of Formula I in which $R_1$ is —$R_2$—C(=O)—NH—NH—$R_3$ and both $R_3$'s are hydrogen, whereby during the biodegradation of the crosslinked polymer network, water-soluble angiogenic compounds are released from the crosslinked polymer network.

It is generally known to use the commercially available hydrazide-functionalized poly(alkylene oxides) such as poly (ethylene glycol) to cross-link polymers. Therefore, for biodegradable polymer chains in general, the present invention does not include polymer networks cross-linked with compounds in which P contains only ethylene oxide repeating units when $R_1$ is —$R_2$—C(=O)—NH—NH—$R_3$ and both $R_3$'s are hydrogen. However, it is not known to cross-link certain specific biodegradable polymers in this manner, and the resulting angiogenic properties are an unexpected result. Therefore the present invention does not exclude P being a poly(alkylene oxide) when the biodegradable polymers are polymerized from L-tyrosine-derived diphenol monomers, such as the diphenol monomers of U.S. Pat. Nos. 5,099,060 and 5,198,507, or L-tyrosine-derived hydroxyacid amides, such as the hydroxyacid amides of U.S. Pat. No. 6,284,862. Instead, the use of poly(alkylene oxides) is preferred, including block copolymers of different alkylene oxide segments. The preferred poly(alkylene oxide) is poly(ethylene glycol). Biodegradable polymers suitable for cross-linking thus include tyrosine-derived polycarbonates, polyimino-carbonates and polyarylates.

In addition to poly(alkylene oxides), other water-soluble polymers suitable for use in the present invention include water-soluble polysaccharides, poly(vinyl alcohols), poly(N-methyl pyrrolidones), poly(ethyloxazolines), polyamines, poly(aminoamides), polypeptides, cellulosics such as carboxymethylcellulose and hydroxyethylcellulose, chondroitin sulfate, heparin, alginates, and proteins such as collagen or gelatin. The water-soluble polymer should have a molecular weight effective to form a hydrogel when used as polymer cross-linking agent.

Angiogenesis is a highly desirable biological response in many applications related to tissue regeneration and tissue engineering. The incorporation of the hydrazide compounds of the present invention into biomaterials can be used to render devices and implants made from such materials inherently angiogenic. These hydrazide-containing biomaterials can be used as coatings or as the main component of medical devices leading to an improved healing response relative to devices and implants prepared from materials that do not contain the hydrazide compounds of the present invention. Without being bound by any particular theory, and without putting forth a formal mechanism to explain why these synthetic molecules are able to modulate endothelial cell activity regarding cell migration and angiogenesis, it is possible that the —$R_2$—C(=O)—NHNH— domain of the degradation products may be responsible.

The angiogenic organic hydrazide compounds of the present invention provide useful crosslinking agents for backbone polymers that after cross-linking can be utilized as coatings, tissue engineering scaffolds, drug delivery systems and other implantable medical devices. The water-soluble polymer segments decrease the surface adhesion of the crosslinked polymer networks of the present invention. Coatings containing water-soluble polymer segments according to the present invention may be prepared that are resistant to cell attachment and provide useful non-thrombogenic coatings on surfaces in contact with blood. Such coatings also resist bacterial adhesion in other medical applications.

The present invention therefore also includes blood contacting devices and medical implants either formed from or having surfaces coated with the cross-linked polymer networks of the present invention. Methods according to the present invention include implanting in the body of the patient a blood-contacting device or medical implant formed from or having a surface coated with the above-described cross-linked polymer networks of the present invention. For purposes of the present invention, "medical devices" are defined as including tissue engineering scaffolds, drug delivery systems.

A more complete appreciation of the invention and many other intended advantages can be readily obtained by reference to the following detailed description of the preferred embodiment and claims, which disclose the principles of the invention and the best modes which are presently contemplated for carrying them out.

BRIEF DESCRIPTION OF THE DRAWINGS

FIG. 2 depicts the crosslinking reaction for preparation of the crosslinked polymer networks according to the present invention;

BEST MODES OF CARRYING OUT THE INVENTION

Figure 1:
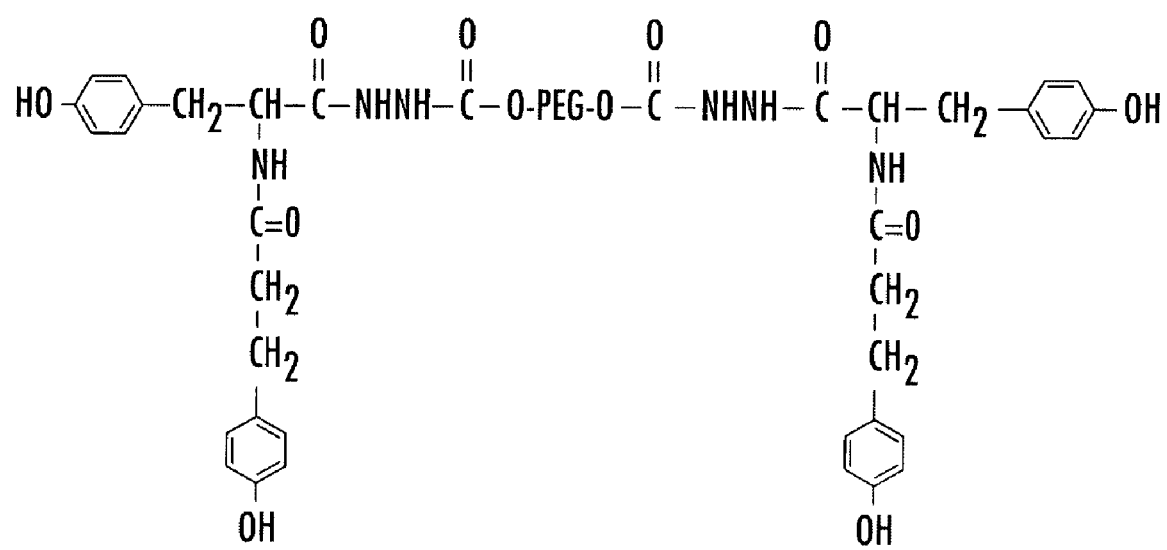
FIG. 1 depicts the structure of an angiogenic PEG-di-DT hydrazide compound according to the present invention.

The present invention provides for hydrophilic polymer hydrazide and dihydrazide compounds that are inherently angiogenic. The compounds of Formula I, including the known compounds in which P is a poly(alkylene oxide), can be used in pure form as low molecular weight angiogenesis-stimulating drugs or they can be incorporated (either by physical mixing or chemical bond) into various biomaterials, imparting angiogenic properties to the biomaterials. When such modified biomaterials are used in the fabrication of devices or implants, such devices and implants will stimulate tissue and blood vessel growth at the implant site leading to an improved healing and/or tissue regeneration response associated with improved patient outcome. Further, the dihydrazide compounds in which $R_1$ is —$R_2$—C(=O)—NH—NH—$R_3$ and both $R_3$'s are hydrogen are effective cross-linking agents for a wide variety of backbone polymers. The crosslinked polymers have, as a consequence of the properties of the dihydrazide cross-linking agents, angiogenic properties as well as hydrogel properties.

Compounds according to the present invention thus include compounds of Formula I in which P, $R_1$, $R_2$ and $R_3$ are the same as described above for Formula I. Lower alkyl and lower alkoxy are defined as containing from one to six carbon atoms and preferably one or two. Suitable water-soluble polymers include water-soluble polysaccharides, poly(vinyl alcohols), poly(N-methyl pyrrolidones), poly(ethyloxazolines), polyamines, poly(amino-amides), polypeptides, cellulosics such as carboxymethylcellulose and hydroxyethylcellulose, chondroitin sulfate, heparin, alginates, and proteins such as collagen or gelatin. The water-soluble polymer should have a molecular weight effective to form a hydrogel when used as polymer cross-linking agent, typically between about 250 and about 50,000.

The preferred water-soluble polymer is a poly(alkylene oxide), with poly(ethylene glycol) (PEG) being the preferred poly(alkylene oxide). PEG, when used, preferably has a molecular weight between about 1000 and about 5000.

The process by which hydrazides may be terminally attached to water-soluble polymers is well known and demonstrated in the examples. As noted above, such products in which the water-soluble polymer is a polyalkylene oxide are commercially available. To the extent poly(alkylene oxide) mono- or bis-hydrazides are know, such compounds are excluded from the scope of subject matter claimed by the present invention.

Hydrazide compounds in which at least one alpha-L-amino acid residue or dipeptide thereof is attached via the hydrazide to a water soluble polymer are also included among the angiogenesis promoting polymers of the present invention. The process by which this may be done is essentially conventional and also depicted in the Examples. For purposes of the present invention, "amino acid residues and dipeptides thereof" are defined as including the L-tyrosine-derived diphenol monomers of U.S. Pat. Nos. 5,099,060 and 5,198,507, and the L-tyrosine-derived hydroxyacid amides of U.S. Pat. No. 6,284,862.

The hydrogel polymer networks of the present invention are also formed by conventional cross-linking reactions between biodegradable backbone polymers and compounds of Formula I which are cross-linking agents, i.e., $R_1$ is —$R_2$—C(=O)—NH—NH—$R_3$ and both $R_3$'s are hydrogen. This is shown in FIG. 2, in which the cross-linker, PEG-dihydrazide, is attached to a variety of poly(DTE-co-X % DT carbonates) with EDCI. The chosen nomenclature defines the hydrogels by the DT content followed by the degree of crosslinking of the entire polymer chain (not just the chains available for crosslinking). For example, 50/40 represents a hydrogel composed of poly(DTE-co-50% DT carbonate), where 40% of the entire polymer chain is crosslinked (but 80% of the DT pendent chains are crosslinked). This is also demonstrated in the Examples.

Preferred backbone polymers include the L-tyrosine-derived polycarbonates and polyiminocarbonates disclosed by U.S. Pat. Nos. 5,099,060 and 5,198,507, the L-tyrosine-derived polyarylates described in U.S. Pat. No. 5,216,115 and the poly(alkylene oxide) block copolymers with the aforementioned polycarbonates and polyarylates disclosed in commonly owned U.S. Pat. No. 5,658,995. The polymers disclosed by U.S. Pat. No. 6,284,862 prepared from hydroxy acid amides of L-tyrosine are also preferred.

A preferred class of angiogenic, biodegradable hydrogels are produced, comprising backbone polymers of polycarbonates, polyiminocarbonates, polyarylates, and poly(alkylene oxide) block copolymers thereof, which are based on L-tyrosine and its derivates, and which are crosslinked with poly(alkylene oxide)-dihydrazides.

Methods for preparing the diphenol monomers of the preferred backbone polymers containing as part of their structures a carboxylic acid ester group are disclosed in commonly owned U.S. Pat. Nos. 5,587,507 and 5,670,602, the disclosures of both of which are hereby incorporated by reference. The preferred desaminotyrosyl-tyrosine esters are alkyl or aralkyl groups containing from 1 to 18 carbon atoms and more preferably are ethyl, butyl, hexyl, octyl and benzyl (DTBn) ester groups. For purposes of the present invention, desaminotyrosyl-tyrosine ethyl ester is referred to as DTE, desaminotyrosyl-tyrosine benzyl ester is referred to as DTBn, and the like. For purposes of the present invention, the non-ester desaminotyrosyl-tyrosine free carboxylic acid is referred to as DT.

Block copolymers of tyrosine based polycarbonates and poly(alkylene oxide) are disclosed in commonly owned U.S. Pat. No. 5,658,995, and block copolymers of tyrosine based polyarylates and poly(alkylene oxide) are disclosed in commonly owned U.S. Pat. No. 6,048,521 and U.S. Pat. No. 6,319,492, the disclosure of which is also incorporated herein by reference. These copolymers are useful as backbone polymers of the present invention.

The hydrogels of the present invention also find application in areas where both solid materials and solvent-soluble materials are commonly employed. Such applications include polymeric scaffolds in tissue engineering applications and medical implant applications. The incorporation of polyalkylene oxide blocks decreases the adhesiveness of the polymeric surfaces, making them resistant to cell and bacterial attachment and may be useful as non-thrombogenic coatings on surfaces in contact with blood. The porous polymer scaffold devices of U.S. Pat. No. 6,103,255 can be prepared using the angiogenic organic hydrazide compounds of the present invention. Alternatively, porous polymer scaffolds can be prepared by dispersing fine particles of an insoluble salt that is eluted using a solvent in which the salt is soluble but the polymer is not. Shaped articles may be prepared from the polymers of the present invention for medical implant and drug delivery applications. The present invention thus includes implantable devices prepared from the organic hydrazide cross-linked polymers of the present invention and the use of these devices to stimulate angiogenesis as a primary or secondary objective.

These hydrazide compounds have been extensively tested both in animal and cell models. In vitro, the pure PEG-di-DT hydrazide (FIG. 1) has been tested in an endothelial cell migration assay. In this assay, endothelial cells (a major component of blood vessels) demonstrated a migration response similar to the response elicited by FGF-β, a known angiogenic substance. In vivo, a novel dihydrazide compound was used as a cross-linker to form hydrogel sponges. These sponges were implanted subcutaneously in rats and demonstrated biocompatibility and increased vascularization over the life of the device. In vivo and in vitro angiogenesis-stimulating methods are thus included within the scope of the present invention.

A novel class of angiogenic, biodegradable hydrogels is disclosed herein in which the backbone precursor polymers are tyrosine-derived polycarbonates, polyimino-carbonates or polyarylates and the crosslinking agents are poly(alkylene oxide) dihydrazides derivatives. The backbone polymers are therefore hydrophobic and mechanically strong, while the crosslinking agents are hydrophilic. Consequently, a wide range of hydrogel properties are obtained by varying the chemical compositions and mole ratios of the backbone polymers and crosslinking agents.

A series of structurally similar tyrosine-derived polycarbonate hydrogels were prepared in which polyethylene glycols (PEG) were the crosslinking agents. In these hydrogels, the backbone polymers' desaminotyrosine (DT) content varied from 10-100% and the crosslink density was varied from 8-80%. Hydrogels were fabricated via solvent-casting into either porous scaffolds or non-porous films, depending on the characterization assay. In these hydrogels, the polymer backbone consisted of degradable polycarbonates derived from the amino acid tyrosine. Tyrosine-derived polycarbonates were previously shown to be tissue-compatible, strong, tough, hydrophobic polymers with slow degradation rates. In particular, poly(DTE carbonate) was a good substratum for cell growth in vitro, and demonstrated a high degree of bone biocompatibility in both canine and rabbit models.

The incorporation of free carboxylate pendent chains into tyrosine-derived polycarbonates was shown to increase the degradation rate. A series of carbonate copolymers of desaminotyrosine ethyl ester (DTE) and DT with the general formula poly(DTE-co-X % DT carbonate) was prepared, with the DT content ranging from 5 mole % to 100 mole %. The presence of free carboxylate pendent chains in poly (DTE-co-X % DT carbonate) provided an opportunity to transform these strong and relatively hydrophobic materials into hydrogels by crosslinking the polymer with poly(ethylene oxide) (PEG) (FIG. 2). PEG was chosen for its lack of toxicity, immunogenicity and ease of excretion from the body and was a commonly used component in the design of synthetic hydrogels. To facilitate the crosslinking reaction between PEG and the carboxylate groups of the polymer backbone, the hydroxyl end groups of PEG were modified to hydrazide groups. This approach resulted in a stable crosslink between degradable polymer backbone chains (Scheme 2), leading to the formation of PEG-di-DT-hydrazide as one of the hydrogel degradation products.

The design of tyrosine-based PEG-hydrazide crosslinked hydrogels provides for four independent parameters which can be varied over a wide range. The first parameter is the amount of free carboxylate pendent groups (designated as DT in the polymer structural formula), which can be varied from 0% to 100%, indicating that none or all of the polymer repeat units carry a carboxylate group. The second parameter is the theoretical crosslink density (TCD), determined by the amount of PEG-di-hydrazide added to the reaction mixture during the crosslinking reaction. When, for example, poly (DTE-co-50% DT carbonate) is selected as the base polymer, wherein 50 mole % of all polymer repeat units are DT and 50 mole % are DTE, and the crosslinking reaction is performed using an amount of PEG-di-hydrazide equivalent to 40 mole % relative to the number of repeat units of poly(DTE-co-50% DT carbonate) present in the reaction mixture, the resulting hydrogel has a PEG-di-hydrazide crosslink at 40 mole % of all repeat units and a residual amount of 10 mole % of the repeat units still carries a reactive carboxylate group (DT). The third parameter is the molecular weight of the PEG chain used in the crosslinking reaction. Finally, the fourth parameter is the structure of the alkyl ester pendent chain of the ester monomer; there is a wide range of useful alkyl esters, referred to generally as "DTX," and more specifically, for example, as ethyl (DTE), butyl (DTB), hexyl (DHT), and octyl (DTO) esters.

The hydrophilic polymer hydrazide and dihydrazide compounds of the present invention find utility as angiogenesis stimulating compounds without being used as hydrogel cross-linkers. Thus the present invention also includes non-hydrogel compositions containing the hydrophilic polymer hydrazide and dihydrazide compounds of the present invention. Compositions for stimulating angiogenesis systemically or site-specifically are provided in which effective quantities of the non-hydrogel compounds of the present invention are combined with a pharmaceutically acceptable carrier. Such compositions include biocompatible polymers blended with an effective amount of the hydrazide and dihydrazide compounds. The present invention also includes angiogenesis-stimulating methods using the non-hydrogel angiogenesis-stimulating compounds and compositions of the present invention. However, the hydrogel compositions of the present also possess the same utility.

The angiogenesis-stimulating methods of the present invention using either angiogenic polymer hydrogels or non-hydrogel hydrazides and dihydrazides thus include both in vivo and in vitro methods. In vitro methods are employed, for example, to generate vasculature in implanted tissue. In vivo methods use the compounds of the present invention to study angiogenesis in the design of tissue implants and scaffolds for tissue engineering and also to promote angiogenesis as a means of studying how it may be hindered, for example, in the development of anti-tumor compounds and methods of treatment.

The following non-limiting examples set forth herein below illustrate certain aspects of the invention. All parts and percentages are by mole percent unless otherwise noted and all temperatures are in degrees Celsius. All solvents were HPLC grade. All other reagents were of analytical grade and were used as received.

EXAMPLES

The monomers desaminotyrosine-tyrosine ethyl ester (DTE) and benzyl ester (DTBn) were prepared using published procedures. Poly(DTE-co-X % DT carbonate)s were synthesized as previously described. In general, DTE and DTbenzyl (DTBn) were co-polymerized by phosgenation. Then, using hydrogen over 5% Pd on $BaSO_4$ in DMF, the resulting poly(DTE-co-X % DTBn carbonate) was hydrogenated to obtain the corresponding poly(DTE-co-X % DT carbonate).

Example 1

Preparation of Peg-Dihydrazide

PEG (Mw=2000, 100 g, 0.05 mol) and toluene (1 L) were dried by azeotropic distillation of a toluene solution using a Dean-Stark adapter. After cooling, a 20% solution of phosgene in toluene (150 mL) was added to the flask and stirred overnight to obtain PEG-dichloroformate. Excess phosgene was distilled off along with toluene. Then, methylene chloride (100 mL) and dry toluene (300 mL) were added to the residue followed by N-hydroxysuccinimide (NHS) (17 g, 0.15 mol) and triethylamine (TEA) (15 g, 0.15 mol), and stirred at 0° C. After 2 h, hydrazine (15.7 mL, 0.50 mol) was added and the reaction mixture was stirred for an additional 12 h. The white precipitate of TEA.HCl was removed by filtration, the filtrate was concentrated to a volume of 200 mL and then PEG-dihydrazide was precipitated with 600 mL of diethyl ether. The desired product was isolated by suction filtration, recrystallized from isopropanol (IPA) (800 mL) and then dried under vacuum at room temperature. The product structure and purity were determined by $^1$H NMR.

Example 2

Crosslinking Reaction of PEG-Dihydrazide and poly(DTE-co-X % DT Carbonates)

The crosslinked materials were prepared by reacting a variety of poly(DTE-co-X% DT carbonate)s with PEG-dihydrazide to form porous scaffolds or non-porous films. To prepare a film, the polymer (2 g) was dissolved in 1-methyl-pyrrolidinone (NMP) (20 mL) and PEG-dihydrazide was added in various amounts as shown in Table I:

TABLE I

Amounts of PEG-dihydrazide (peg-diH) and EDCI required to fabricate different hydrogels

| % DT content | % crosslinks | PEG-diH (mg) (Sponge) | EDCI (mg) (Sponge) | PEG-diH (mg) (Film) | EDCI (mg) (Film) |
|---|---|---|---|---|---|
| 10 | 8 | 67 | 12 | 446 | 80 |
| 15 | 12 | 101 | 18 | 670 | 120 |
| 20 | 16 | 135 | 24 | 900 | 162 |
| 25 | 5 | 84 | 15 | 282 | 51 |
| 25 | 20 | 168 | 30 | 1130 | 203 |
| 50 | 20 | 172 | 31 | 1140 | 207 |
| 100 | 20 | 179 | 32 | 1200 | 215 |
| 100 | 80 | 716 | 129 | 4770 | 862 |

Corresponding amounts of N-ethyl,N'-dimethylaminopropyl carbodiimide.HCl (EDCI) were pre-dissolved in methylene chloride (0.5 mL) and added to the reaction mixture, and the reaction mixture was vigorously stirred for 2 minutes. The resulting viscous solution was poured into a Teflon mold (10 cm×10 cm) and allowed to gel into a film. EDCI, a water-soluble carbodiimde, was used since its reaction byproducts are water soluble and easily removed by water extractions. Since the hydrogels can be varied in their DT content as well as their extent of crosslinking, a series was created which varied in DT content from 5%-100%, as well as the amount of crosslinking. The chosen nomenclature defines the hydrogels by the DT content followed by the degree of crosslinking of the entire polymer chain (not just the chains available for crosslinking). For example, 50/40 represents a hydrogel composed of poly(DTE-co-50% DT carbonate) where 40% of the entire polymer chain is crosslinked (but 80% of the DT pendant chains are crosslinked). The least crosslinked device capable of gelation was a 5/5 film. Crosslinked devices of 10/2, 15/3 and 20/4 were unable to induce gelation of the device due to insufficient cross-links. All highly crosslinked devices were capable of gelation.

Example 3

Preparation of Peg-di-Dt Hydrazide

DT (1.5 g, 4.50 mmol), the PEG-dihydrazide of Example 1 (5 g, 2.36 mmol), NMP (10 mL) and HOBt (0.06 g, 0.45 mmol) were placed in a 250 mL round-bottom flask, and formation of a white paste was observed immediately. Methylene chloride (50 mL) was added and the reaction mixture was stirred in an ice-water bath. After 1 h, EDCI (0.9 g, 4.72 mmol) was added and stirring was continued. At regular intervals, aliquots of the reaction mixture were withdrawn and analyzed by HPLC for the completion of the reaction. After that, the reaction mixture was sequentially washed with 25 mL of water, 5% sodium bicarbonate, 0.2 M hydrochloric acid, and 20% sodium chloride. The organic phase was then dried over magnesium sulfate, filtered, and evaporated. The resulting oil was dissolved in IPA (50 mL) under heat, and then the product was crystallized at −20° C. The PEG-di-DT hydrazide yellow solid was washed with IPA and dried under vacuum at 40° C. The resultant PEG-di-DT Hydrazide was a water-soluble compound.

Example 4

Porous Scaffolds for Tissue Engineering

To prepare porous scaffolds, the backbone poly(DTE-co-DT)carbonate (0.3 g) was dissolved in NMP (3 mL) and corresponding amounts of PEG-dihydrazide and EDCI/methylene chloride were added (Table 1). After rapidly mixing for 2 minutes, the solution was poured into a Teflon dish (5 cm diameter) containing 10 g of sieved salt (212-425 µm). Solutions were allowed to set overnight to ensure crosslinking. Devices were punched into disks using an 8 mm Acu•Punch (Acuderm inc., Ft. Lauderdale, Fla.) and washed in water to remove both salt and residual solvent. Devices can be either used or dried and stored at −20° C.

Water uptake of the hydrogels was determined on dried specimens of hydrogels that were weighed, incubated in water at room temperature for 48 hours, and re-weighed to obtain wet weight. Water uptake was calculated as the % ratio of weight increase over dry weight.

Compressive modulus was measured on an MTS Sintech 5/D mechanical tester (MTS System Corporation, Eden Prairie, Minn.) equipped with a temperature-controlled waterbath (MTS Model 658.25 Environmental Chamber). The PC controller and data acquisition were run by MTS Testwork4 software. To measure the compressive strength of hydrogel specimens under simulated physiological conditions, the water bath was filled with deionized water and set to 37° C. The sample thickness and diameter were measured in triplicate. Samples were inserted unconfined between two flat platens in the water bath and compressed at a rate of 0.5 mm/min to 90% of their original thickness. Compressive moduli were defined as the initial slope of the generated stress-strain curves.

Figure 3A:
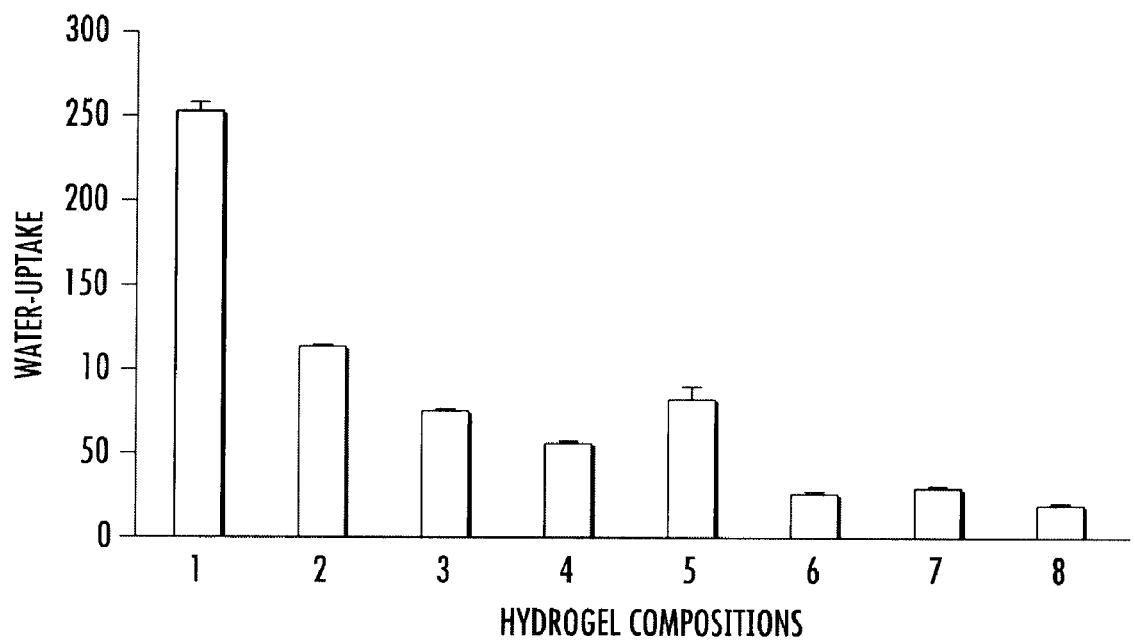
FIG. 3 depicts the water uptake of hydrogels over 6 months for crosslinked polymer networks according to the present invention varying by DT monomer content in the polymer backbone.
Figure 3B:
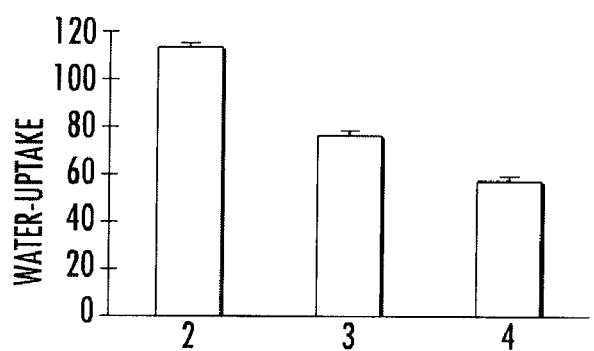

The equilibrium water content (EWC) was related to the chemical composition of the hydrogels. As shown in FIG. 3, PEG content was the most significant determinant of water uptake, most likely due to its considerably hydrophilic nature. The second determinant of water uptake was DT content, as shown in hydrogels which contain the same degree of crosslinking, but different DT contents (i.e. 100/20, 50/20, 25/20). DT was slightly hydrophilic, therefore decreasing the DT content was expected to moderately decrease water uptake. In this case, increasing the cross-links rendered the device more hydrophilic, hence increasing the water uptake. In comparison to similar hydrogel systems in which hydrophobic acrylated poly(ε-caprolactone-co-glycolic acid-co-L-serine) was crosslinked with hydrophilic HEMA (2-hydroxyethyl methacrylate), the maximum water uptake obtained was 38%.

Following water uptake, the porous scaffolds were tested in compression. These results showed a range of moduli of 40-370 kPa±18-58 kPa. Moduli tended to increase with less crosslinking, regardless of the DT content. This is opposite to what is expected with cross-links, which are usually incorporated to stiffen a material. However, increasing the hydrophilic cross-linker softens the material. The porous morphology is probably the main factor contributing to the moduli.

Example 5

Scaffold Degradation Studies

To determine degradation products of porous scaffolds (compositions used: 100/80, 50/40 and 25/20), hydrogel disks of various compositions samples were incubated at 37° C. in SBF at a constant weight to volume ratio of 5 mg/mL, maintaining a constant surface area to volume ratio. Over a one-week period, aliquots were removed and analyzed by HPLC. Buffer solutions were changed every two weeks to maintain sink conditions. Samples were analyzed over a 6-month period for degradation products in the buffer by HPLC, for water uptake by TGA, and mass loss by gravimetry. Aliquots of the degradation media were analyzed by HPLC. The HPLC system consisted of a reversed-phase (C18) column (Perkin-Elmer, Norwalk, Calif.), an LC pump (Model 410; Perkin-Elmer), a UV array detector at 220 nm (Model 235 Perkin-Elmer), an autoinjector (Model ISS-100; Perkin-Elmer), and a computerized data station (Turbochrom; Perking Elmer). A gradient system of water:acetonitrile was used as an eluent to capture each degradation product. Degradation was monitored using DT and DTE standards, and quantitation of degradation products was determined from the area under the signal peaks in the chromatogram after correlating to the standards. For gravimetric measurements, the hydrogel was removed at the indicated time-point, blotted dry, further dried under vacuum for two weeks (to ensure complete water removal) and re-weighed (weight$_{tp}$). Mass loss was calculated as the % ratio of weight lost over initial weight. Alternatively, thermogravimetric analysis was performed with a High-Res TGA 2950 (TA INSTRUMENTS, New Castle, Del.).

In chemical degradation studies, all scaffolds degraded into desaminotyrosine ethyl ester (DTE), desaminotyrosine (DT), and PEG-di-DT hydrazide following incubation in SBF. This indicates that the main mechanism of degradation involves cleavage of the carbonate bonds in the polymer backbone and not cleavage of the cross-linking unit. As expected, the amount of product released from each hydrogel correlated to the degree of crosslinking.

In physical degradation studies, the scaffolds exhibited a wide range of degradation times. Those of high DT content (25%-100% DT) physically degraded between 1-7 days while those of lower DT content (<25% DT) maintained their physical form for 3-6 months. This trend was most likely due to increased water penetration into the scaffold due to the presence of PEG, which resulted in rapid carbonate bond cleavage. Since materials with higher DT content have more chains available for crosslinking, they will be expected to contain more PEG. In addition, since DT is hydrophilic, even a lightly crosslinked scaffold can degrade rapidly due to the presence of uncross-linked DT pendent chains.

Figures 4A, 4B:
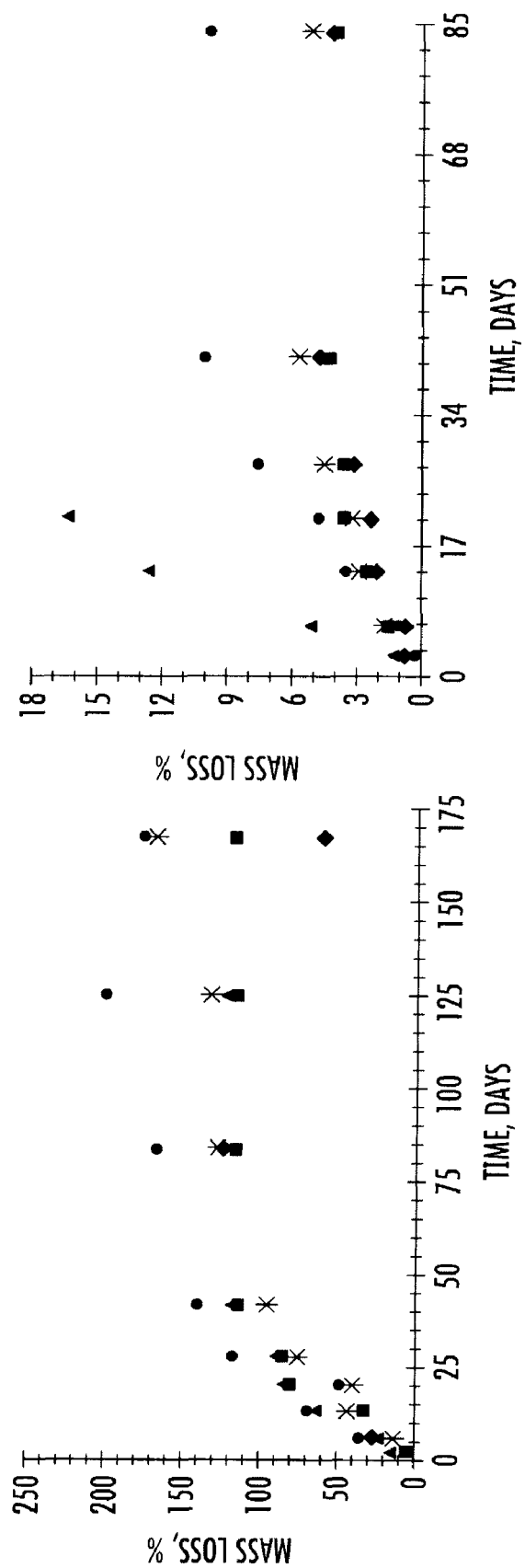
FIG. 4 depicts DT (A) and DTE (B) mass loss for crosslinked polymer networks according to the present invention over a six months degradation study.

Degradation of hydrogels into DT, DTE and PEG-di-DT hydrazide was monitored by HPLC analysis. 100/80 and 100/20 were dissolved before the first time-point, and are generally not included in the graphs. 50/20 was dissolved by 20 days. 25/5 and 25/20 were gone within 6 months. 20/16 and 15/12 remained for the duration of the study and yielded information about the behavior of the three major degradation products. The product DTE was completely undetectable by HPLC by 12 weeks, and the values do not add up to 100% because DTE itself was hydrolyzed into DT during the course of degradation, and additionally it was not being produced anywhere else in the device (FIG. 4).

Figure 5:
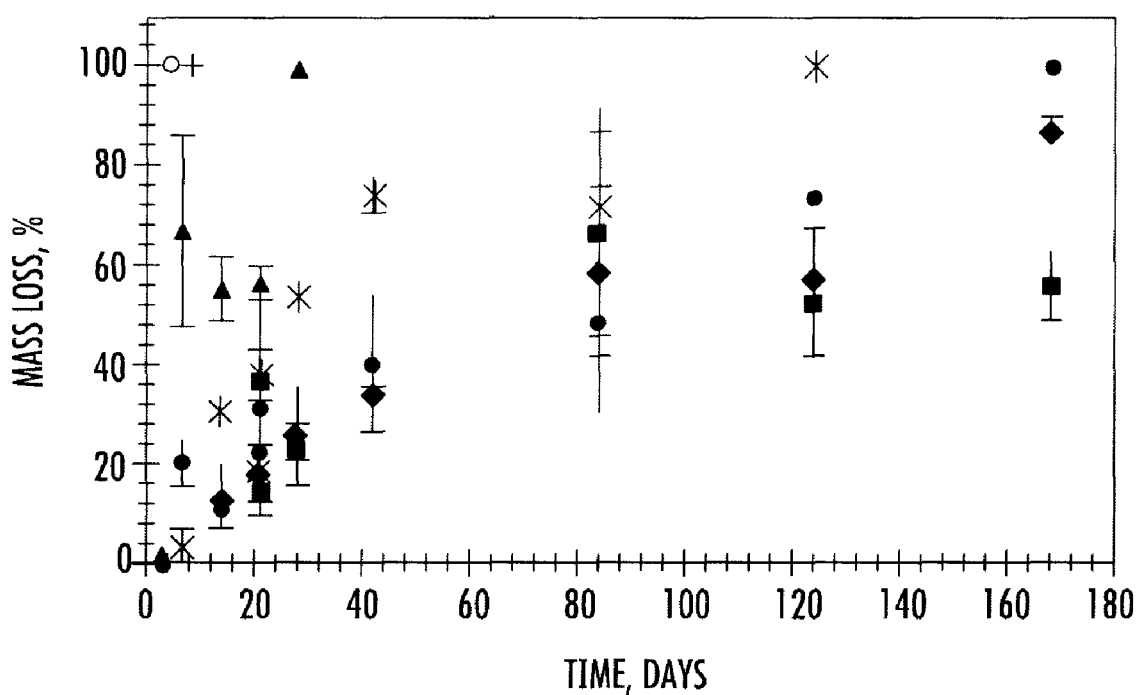
FIG. 5 depicts percent mass loss as measured by gravimetry for the crosslinked polymer networks of FIG. 4.

By contrast, DT continued to remain during the course of degradation. The mass loss profile (FIG. 5) curved into a "hump", then sloped down again before leveling off. The percent mass loss actually was greater than 100% because DT was being produced as a byproduct of DTE hydrolysis, as well as a byproduct of PEG-di-DT hydrazide degradation.

PEG-di-DT hydrazide was undetectable by HPLC by 6 weeks. This compound produced DT as one of its byproducts, hence early massive degradation of PEG-di-DT hydrazide most likely contributed to the "hump" noticed in the DT profile curve. A curve profile based on mass loss was not generated for PEG-di-DT hydrazide since the PEG component could be detected by the ultraviolet detector used for HPLC.

All hydrogel compositions exhibited a surge of water uptake in the early stages of degradation, which dropped at about 6 weeks. This corresponded to the complete degradation of PEG-di-DT hydrazide, which contained the hydrophilic PEG component. Once the PEG degraded out of the hydrogel, water uptake dropped.

Samples showed an increase in mass loss over time. Deviations and large error could be attributed to erosion of the samples during the course of degradation, making complete recovery of the sample for time-point weights difficult. Rate of mass loss was dependent on PEG content, which was the first component to exit the system. Samples with high PEG content, such as the 100% DT or 50% DT hydrogels rapidly eroded. Samples with less PEG content remained viable throughout the duration of the study, but evolved from hydrogel disks into hard "shells" which crumbled under pressure, again due to evacuation of PEG from the system. It was not possible to compare physical mass loss to the values obtained from the three degradation products since the PEG component could be accounted for.

Example 6

In Vitro Cytotoxicity

In vitro biocompatibility studies of PEG-di-DT hydrazide were assessed by analyzing cytotoxicity. Rat lung fibroblasts (RLF-6) and rat osteosarcoma cells (UMR-106) (ATCC, Manassas, Va.) were maintained under typical cell culture conditions (Abramson 2002). Simulated body fluid (SBF) was prepared according to published procedures. The CellTiter96® Aqueous One Solution Cell Proliferation Assay (Promega, Madison, Wis.) was used to determine cytotoxicity. Plates were read on a PowerWave$_x$ absorbance plate reader, (Bio-Tek Instrumentation, Inc., Highland Park, Vt.).

Cell toxicity studies were carried out in 96-well plates made of tissue-cultured polystyrene, and ~3×10$^3$ cells were seeded in each well. Serial dilutions of PEG-di-DT hydrazide were prepared in concentrations ranging from 200 mg/mL to 7.8 mg/mL using SBF as the diluent. Volume of media was kept constant to prevent nutritional advantages. Filter-sterilized dilutions (n=6) were plated in a 96 well plate and controls of media+cells+diluent (to account for affects of the diluent), and media+cells (optimal cell culture conditions) were employed. The experiment also included PEG2000 and sodium lactate as controls. The plates were incubated for 2 hours and read at 490 nm on an absorbance plate reader. Data were analyzed using a two-tailed Student t-test, establishing statistical significance at $p<0.05$ when compared to cells grown in the cell+media+diluent control.

The level of PEG-di-DT hydrazide compared well with PEG2000, a non-toxic substance, and sodium lactate, a substance which can cause toxicity at low concentrations (Table 2). Based solely on dry weights of approximately 15-30 mg, all scaffold compositions except the most crosslinked 100/80 contained 25 mg or less of PEG-di-DT hydrazide. These results suggested that when swollen in an aqueous solution, or implanted in vivo, the concentration of PEG-di-DT hydrazide would decrease (due to an infinite sink conditions), rendering devices fabricated with PEG-di-DT hydrazide even less toxic.

TABLE 2

Results of the Cytotoxicity Assay

| Cell Line | PEG2000 (mg/mL) | Sodium Lactate (mg/mL) | PEG-di-DT Hydrazide (mg/mL) |
|---|---|---|---|
| RFL-6 | 50 | 3 | 12.5 |
| UMR-106 | 25 | N/A | 12.5-25 |

Example 7

In Vivo Biocompatibility

In vivo biocompatibility was determined by implanting the hydrogels into rats for a period of up to 15 weeks. Porous scaffolds of 100/80, 10/8, and non-crosslinked poly(DTE carbonate) were sterilized with ethylene oxide and de-gassed for two weeks. One or three samples of 100/80, measuring ~8 mm in diameter and 1-2 mm thick were implanted subcutaneously into 200-225 g Sprague-Dawley female rats. The surgeries were performed as previously published. The scaffolds were implanted in the left side, and the right side was sham-operated without implants as a control. Rats were sacrificed at either one or three weeks by administration of excess sodium pentobarbital. Four rats were used for each implant/time-point combination. In studies of the 10/8 hydrogels, rats were sacrificed at 1, 3, 8 and 15 weeks, 4 per time-point. Tissue samples were excised, fixed in formalin and sent to Goode Histo Labs for processing and Hemotoxylin and Eosin (H&E) staining of cross-sectional cuts. Processed slides were assessed under light microscopy for inflammation, vasculature, and fibrous capsule formation.

Implants of 100/80 had completely dissolved in vivo before the first time-point, therefore excision of tissue for histology did not include a hydrogel sample. However the tissue reaction was observed both on a gross and microscopic level, as summarized in Table 3.

TABLE 3

Results of the in vivo study to analyze rapidly-degrading (100/80) scaffolds

| Time-point | Implant | Gross Observations | Histological Observations |
|---|---|---|---|
| 1 week | 1 implant | bulky tissue mass (formation of fibrous capsule) | moderate-intense inflammation, very vascular |
| 3 weeks | 1 implant | no sign of inflammation | mild/local inflammation |

TABLE 3-continued

Results of the in vivo study to analyze rapidly-degrading (100/80) scaffolds

| Time-point | Implant | Gross Observations | Histological Observations |
|---|---|---|---|
| 1 week | 3 implants | blood, intense inflammation | very vascular, severe inflammation |
| 3 weeks | 3 implants | no sign of inflammation | mild inflammation, high and low vascularization |

These results indicated that the inflammatory response noted at one week was most likely an acute reaction to the material, particularly the rats implanted with three hydrogels. The implant site in this case was overloaded with material. Additionally, these were highly crosslinked hydrogels which contained large amounts of PEG-di-DT hydrazide. These materials degrade rapidly, (100% mass loss by 3 days) so a burst of degradation materials was released to the site. However, as the material degraded away and the body had time to heal, the inflammation subsided and healthy tissue was formed. It can be concluded that under these circumstances, the inflammatory response noted was not unusual. The time-points were short, and the implant site in some cases was overloaded with material. Even though the initial response was severe, the inflammation eventually subsided to "normal."

In order to study the in vivo response on a longer time scale, slower degrading scaffolds of 10/8 were implanted. Table 4 summarizes these results. Again, an initial moderate inflammatory response was observed at the one-week time-point, characterized by numerous blood vessels and inflammatory cells. However, as time progressed over the 15-week period, new tissue infiltrated the degrading scaffolds and the inflammation subsided, however blood vessels persisted. At one week, blood vessels were noted at the periphery as well as numerous purple nuclei characteristic of inflammatory cells. There was very little tissue infiltration due to little hydrogel degradation. By three weeks, healthy connective tissue denoted by the pink coloring, was infiltrating the degrading scaffold, and blood vessels were noted in the islands of tissue. This trend continued through 15 weeks, when bridges of tissue had begun to form.

TABLE 4

Results of the in vivo study to analyze slowly-degrading (10/8) scaffolds

| Time-point | Histological Observations |
|---|---|
| 1 week | Cell infiltration at periphery, high levels of vascularity, mild to moderate inflammatory response |
| 3 weeks | Significant cell and tissue in growth, vasculature noted, some tissue maturation, ECM, some giant cells(not unusual for 3 weeks) |
| 8 weeks | Moderate inflammation, a lot of blood vessels, islands of tissue filling pores with lots of vessels |
| 15 weeks | Tissues have significant vasculature, less inflammation, still some islands of tissue indicative of incomplete degradation |

These results indicate that the PEG-containing scaffolds could have angiogenic properties. Although blood vessels are usually noted with an inflammatory response, the hydrogels in this study continued to promote vessel growth after the initial inflammatory response subsided.

Example 8

Angiogenesis

To demonstrate that the vasculature in Example 7 was not just from inflammation, an in vitro endothelial cell migration assay was conducted. Endothelial cells were known to respond to angiogenic factors which cause motility and mitosis, and ultimately the release of growth factors from the cells. Human aortic endothelial cells (HAEC) were cultured at passage 8 and maintained and fed with MCDB 131 media with EGM-2 (Clonetics) until the day of the experiment. Cultures were maintained at 37° C., 5% $CO_2$ and 100% humidity. Comparisons were made of PEG-di-DT Hydrazide activity versus basic FGF-β. The PEG-di-DT hydrazide and basic FGF-β were dissolved in MCDB 131 media. Basic FGF-β was used as a positive control due to its well documented angiogenic activity and extensive testing. Dose-response curves were obtained for PEG-di-DT Hydrazide and basic FGF-β. PEG-dihydrazide, DT monomer, and PEG (Mw=2000), were prepared in MCDB 131 media according to Table 2, and were also tested. Migration assays were performed in a 24-well microchemotaxis chamber (Co-Star) containing transwells of untreated polycarbonate membranes with 8 µm pores. Both the transwells and well bottoms were coated overnight with a 10 µg/mL fibronectin solution (Calbiochem). HAE cells were harvested and resuspended at a concentration of $4.5×10^5$ cells/0.1 mL in the corresponding medium. Media was also tested to determine baseline chemotaxis. The bottom wells were filled with 500 µL of test solution, and the transwells were seeded with 4.5×1 cells and incubated for 6 hours at 37° C. The cells that migrated through the membrane were quantitated by counting the whole area of the filter using a grid and a (Olympus) microscope at 40× or 20× magnification. The high concentration of PEG-di-DT hydrazide correlated to the amount in the hydrogel composition which exhibited angiogenesis in vivo, and a lower concentration was chosen to determine the threshold of activity.

Figure 6:
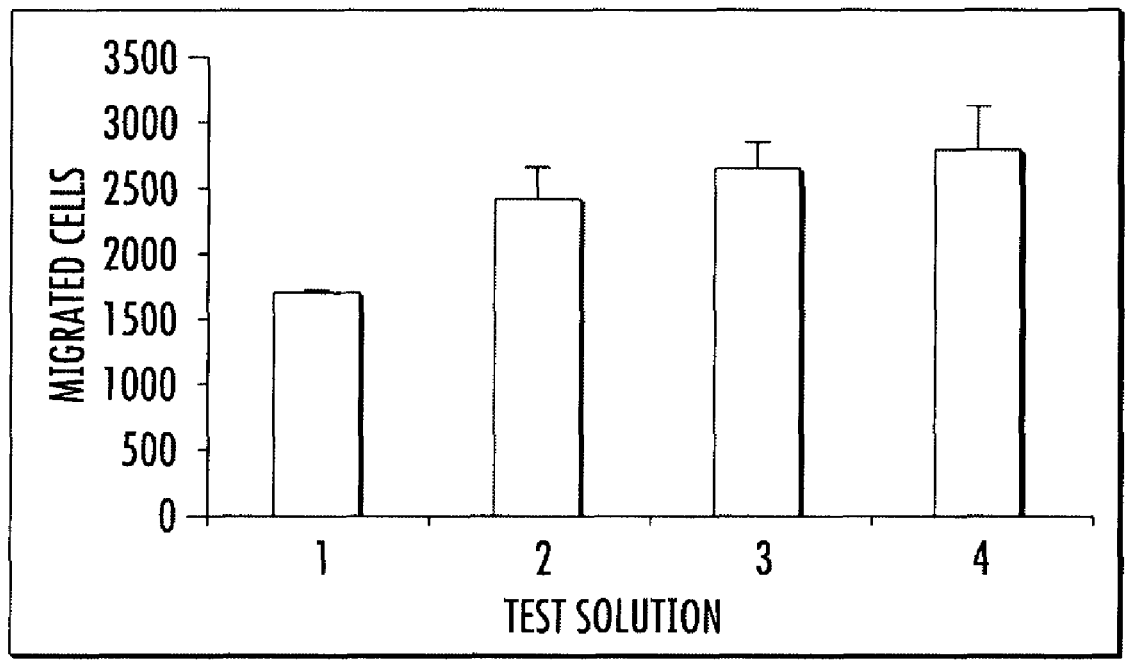
FIG. 6 depicts the activity PEG-di-DT hydrazide according to the present invention and depicted in FIG. 1 compared to FGF-β ((1) media; (2) 0.01 μg/mL FGF-β; (3) 1 μg/mL PEG-di-DT hydrazide; (4) 1000 μg/mL PEG-di-DT hydrazide)
Figure 7:
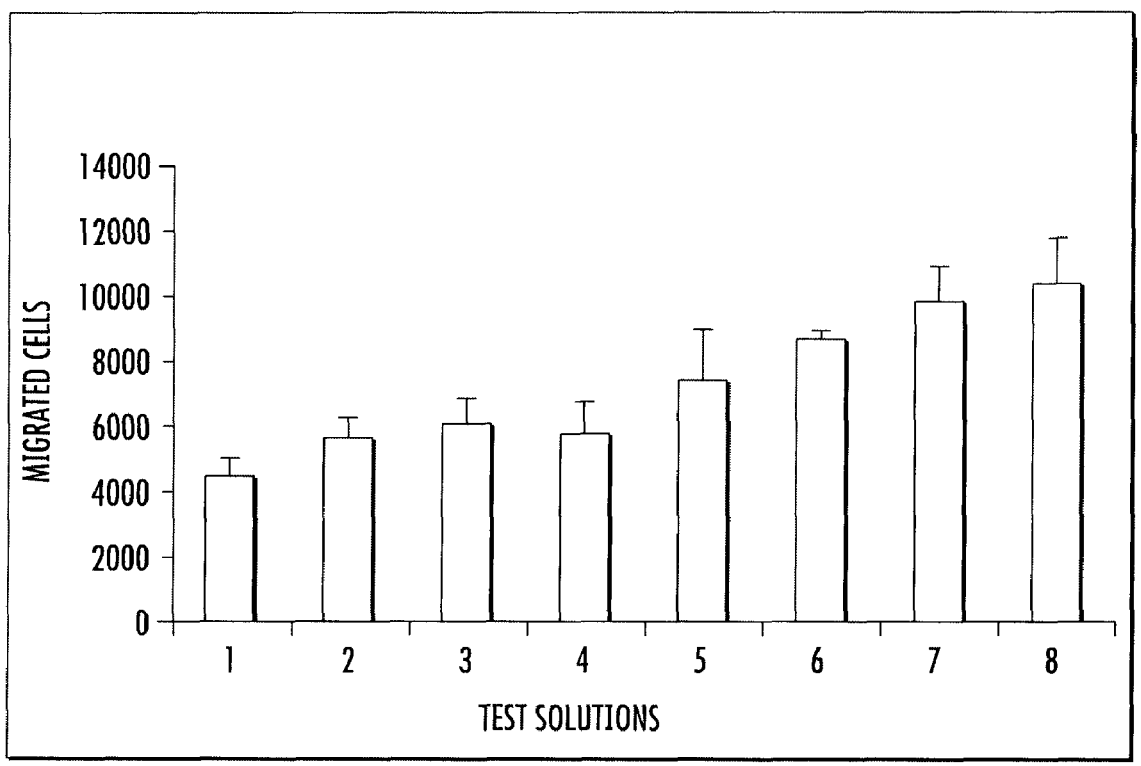
FIG. 7 depicts an angiogenic dose-response curve for the PEG-di-DT hydrazide according to the present invention depicted in FIG. 1 ((1) media; (2) 0.01 μg/mL; (3) 1 μg/mL; (4) 10 μg/mL; (5) 100 μg/mL; (6) 1000 μg/mL; (7) 5000 μg/mL; (8) 10,000 μg/mL)
Figure 8:
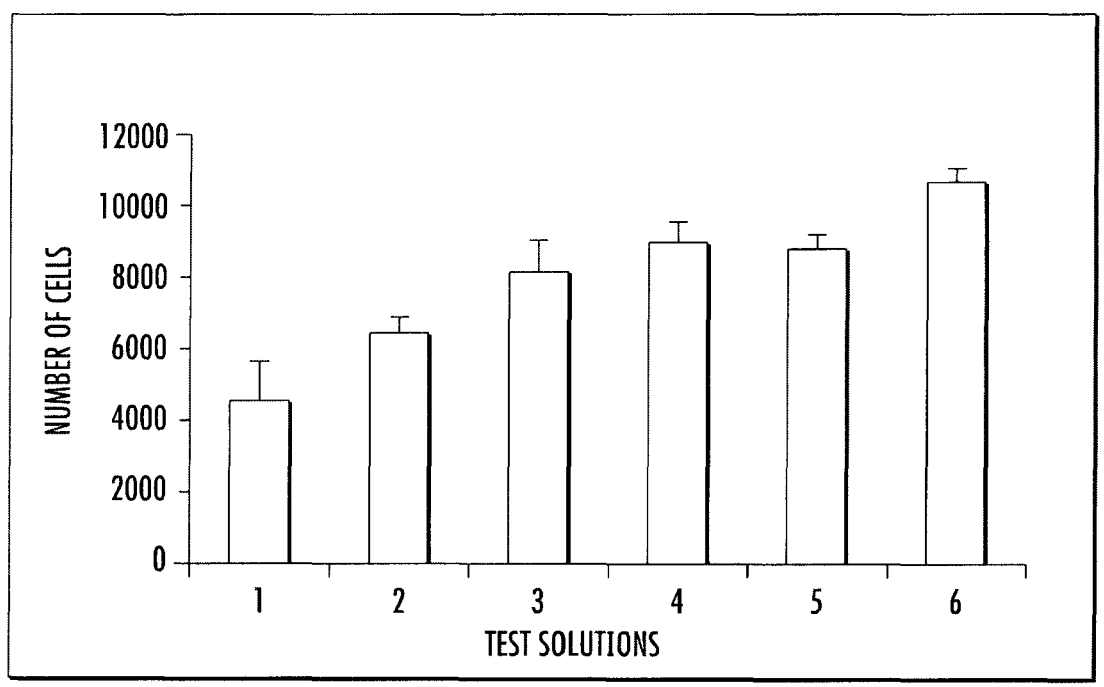
FIG. 8 depicts the angiogenic dose response curve for basic FGF-β for purposes of comparison to FIG. 7 ((1) media; (2) 0.0001 μg/mL; (3) 0.001 μg/mL; (4) 0.01 μg/mL; (5) 0.05 μg/mL; (6) 0.1 μg/mL).

The PEG-di-DT hydrazide produced equivalent cell migration to FGF-β (FIG. 6). Under these assay conditions, the minimum effective concentrations of FGF-β and PEG-di-DT hydrazide were 0.01 and 1 µg/mL respectively. All PEG-di-DT hydrazide and FGF-β concentrations elicited a higher cell migration response than the media alone. For the PEG-di-DT hydrazide solutions, increasing sample concentration led to a dose dependent response regarding cell migration (FIG. 7). The baseline values for the media in the FGF-β chemotaxis assay were similar to the media values in the PEG-di DT hydrazide migration study. The endothelial cells responded to increasing FGF-β concentrations in a dose dependent manner (i.e. there was a smooth trend of increasing cell number for increasing FGF-β concentration) (FIG. 8). A seemingly plateau-like region was observed starting at the 0.001 ug/ml extending up to the 0.1 ug/ml concentration, but none of the plateau region cell number results were statistically different from each other. All of the FGF-β concentrations promoted statistically higher cell migration compared to the media. Neither PEG 2000 nor DT solutions caused cell migration to occur, however, PEG-di-hydrazide solutions induced significant cell migration. Furthermore, cell migration results for PEG di-DT hydrazide coincided with the amount of cell migration induced by the PEG-dihydrazide degradation product for the same concentrations of solutions (FIG. 8). Most of the angiogenic properties of the PEG-di-DT hydrazide were preserved in the PEG-dihydrazide component.

The foregoing examples thus demonstrate the angiogenic properties of the hydrazide compounds of the present invention. The foregoing examples and description of the preferred embodiment should be taken as illustrating, rather than as limiting, the present invention as defined by the claims. Numerous variations and combinations of the features set forth above can be utilized without departing from the present invention as set forth in the claims and all such modifications are intended to be included within the scope of the following claims.

What is claimed is:

1. A compound exhibiting angiogenic properties comprising the structure of Formula I:

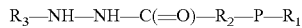

$R_3$—NH—NH—C(=O)—$R_2$—P—$R_1$ wherein P is a water-soluble, biodegradable polymer, $R_1$ is $R_2$—C(=O)—NH—NH—$R_3$; each $R_2$ is independently —$CH_2$—, —NH— or O; and each $R_3$ is desamino-tyrosyl-tyrosine or a desamino-tyrosyl-tyrosine ester.

2. The compound of claim 1, wherein P is a water soluble, biodegradable polymer having a molecular weight between about 250 and about 50,000.

3. The compound of claim 1, wherein P is a water-soluble polymer selected from the group consisting of water-soluble polysaccharides, poly(alkylene oxides), poly(vinyl alcohols) and poly(N-methyl pyrrolidones).

4. The compound of claim 1, wherein P is a poly(ethylene glycol) having a molecular weight between 1000 and about 5000.

5. An implantable medical device comprising the angiogenic compound of claim 1.

6. An implantable medical device coated with the angiogenic compound of claim 1.

7. A method for treating a wound in a patient in need thereof comprising administering at the site of said wound an angiogenically effective amount of the compound claim 1.

* * * * *